United States Patent [19]

Lohr, Jr.

[11] 4,347,742

[45] Sep. 7, 1982

[54] EVALUATING SPRAYABILITY

[75] Inventor: Joseph E. Lohr, Jr., Hoffman Estates, Ill.

[73] Assignee: Stepan Chemical Company, Northfield, Ill.

[21] Appl. No.: 191,901

[22] Filed: Sep. 29, 1980

[51] Int. Cl.³ ............................................. G01N 33/00
[52] U.S. Cl. ................................................ 73/432 SD
[58] Field of Search .............. 73/432 SD, 432 R, 61.4

[56] References Cited

U.S. PATENT DOCUMENTS 2,810,606 10/1957 Taylor ......................... 73/432 R X Primary Examiner—Anthony V. Ciarlante
Assistant Examiner—Joseph W. Roskos

[57] ABSTRACT

Apparatus and processes are provided for evaluating on a miniature scale the sprayability behavior of a specific sprayable aqueous composition. The data acquired through the utilization of such apparatus and processes enables one to predict the behavior of such a composition when used in selected full scale spray equipment. Such a composition is testable for mixability with water, for sprayability when so mixed, and for sprayable composition homogeneity. Correlation between evaluation apparatus nozzle size and full scale spray equipment nozzle size is achievable, so that a given such composition can be reformulated if desirable based upon results obtained from such tests.

15 Claims, 13 Drawing Figures

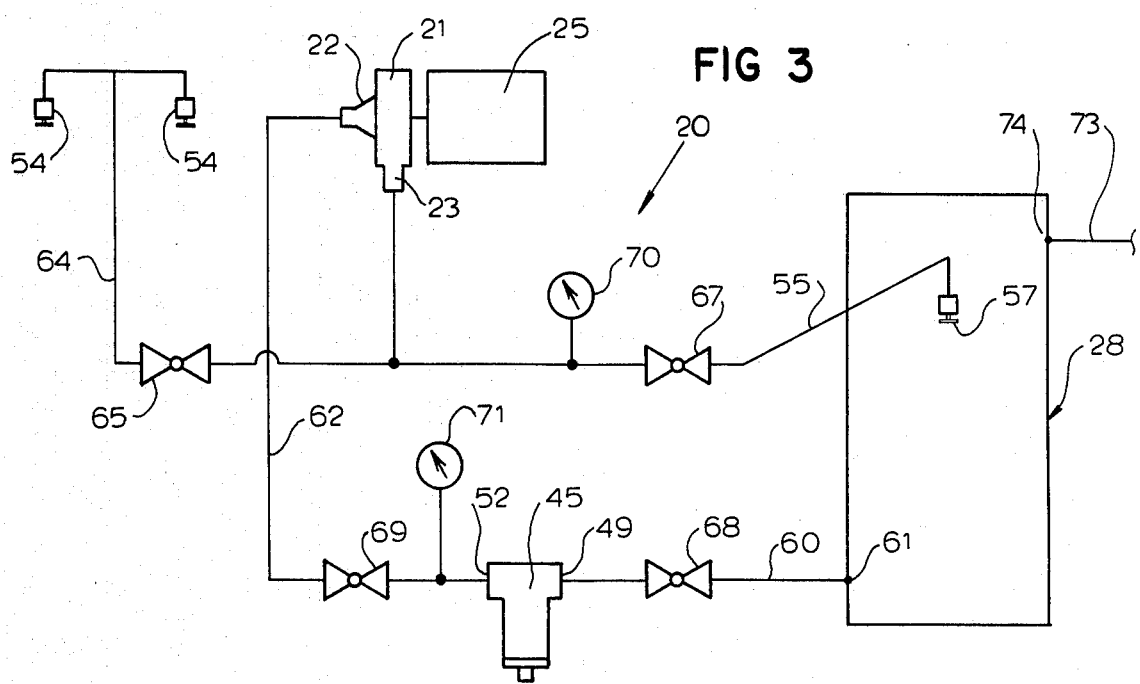
FIG 3
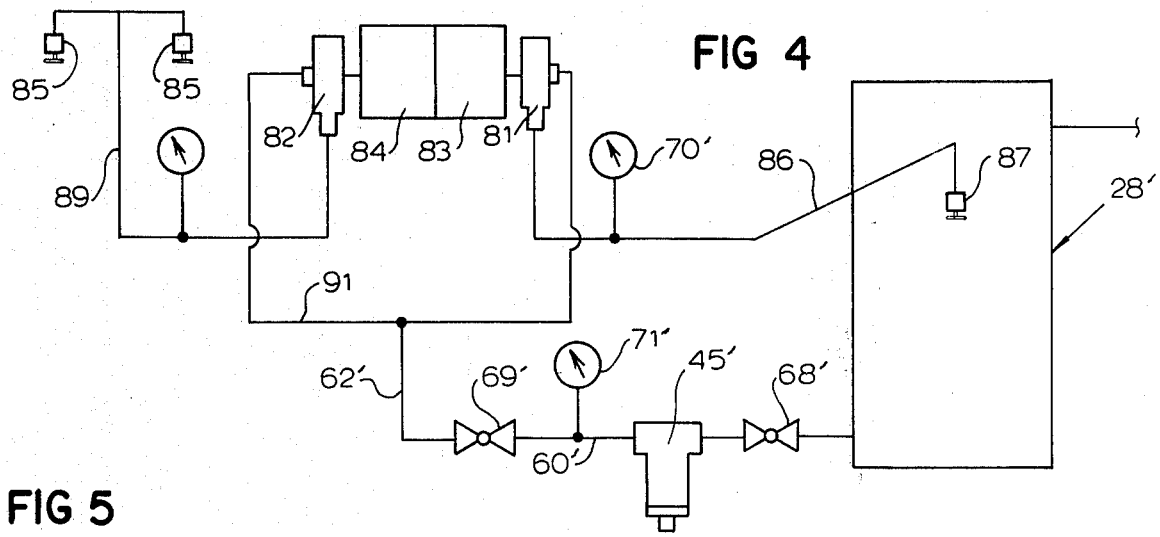
FIG 4
FIG 5
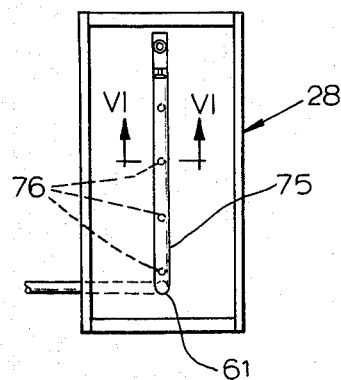
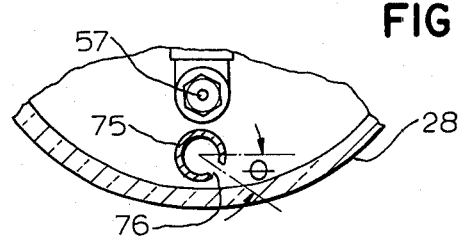
FIG 6

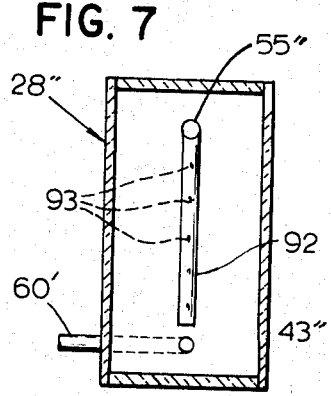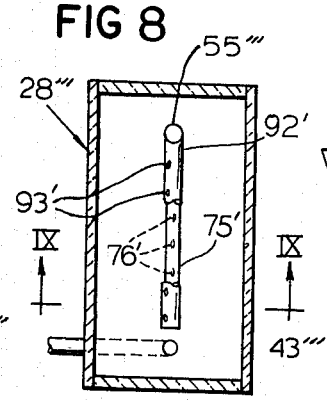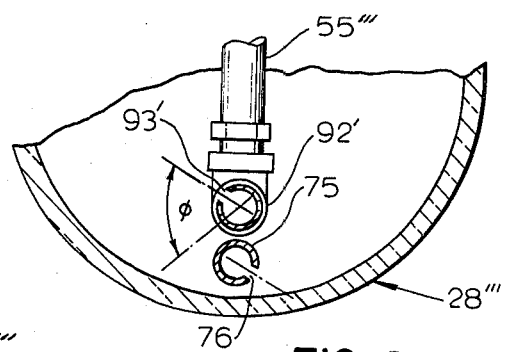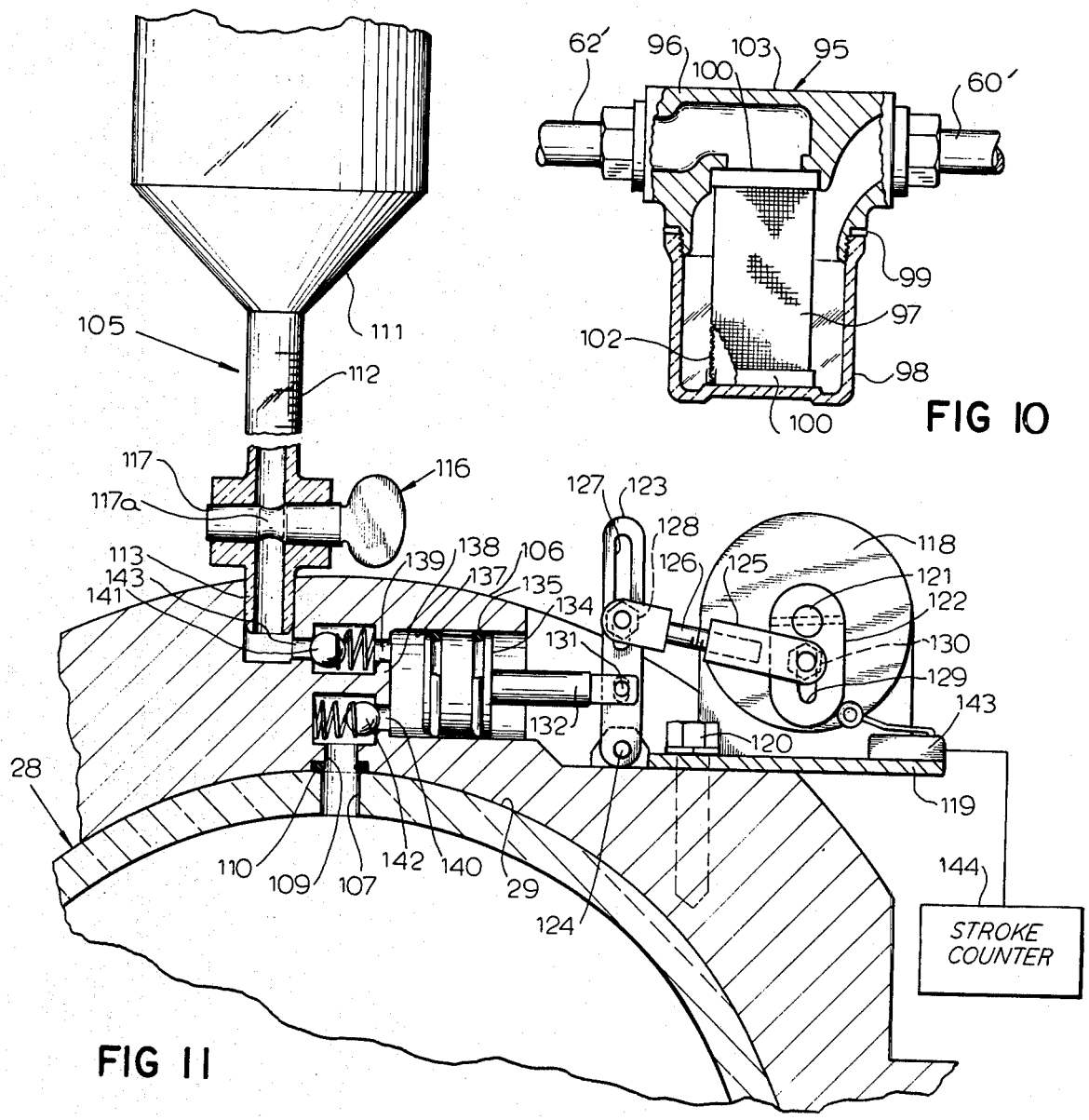

FIG. 12
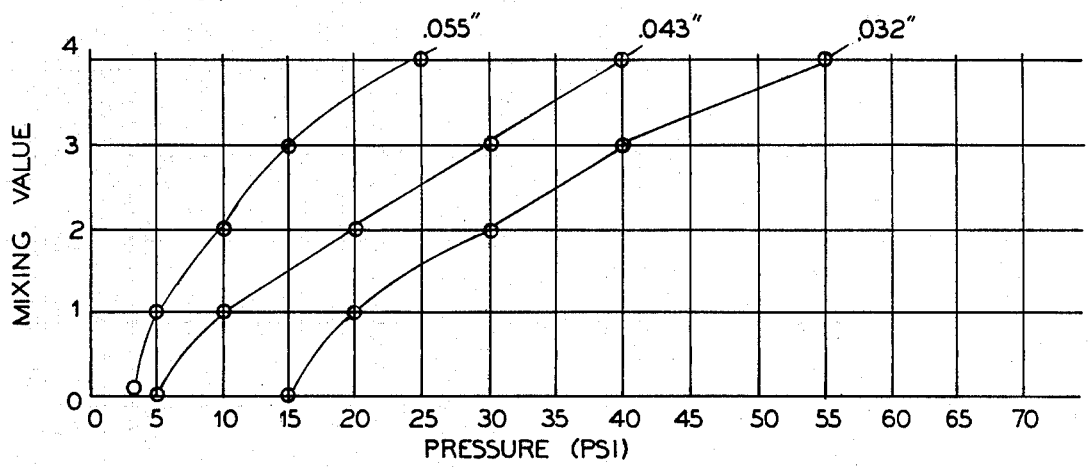
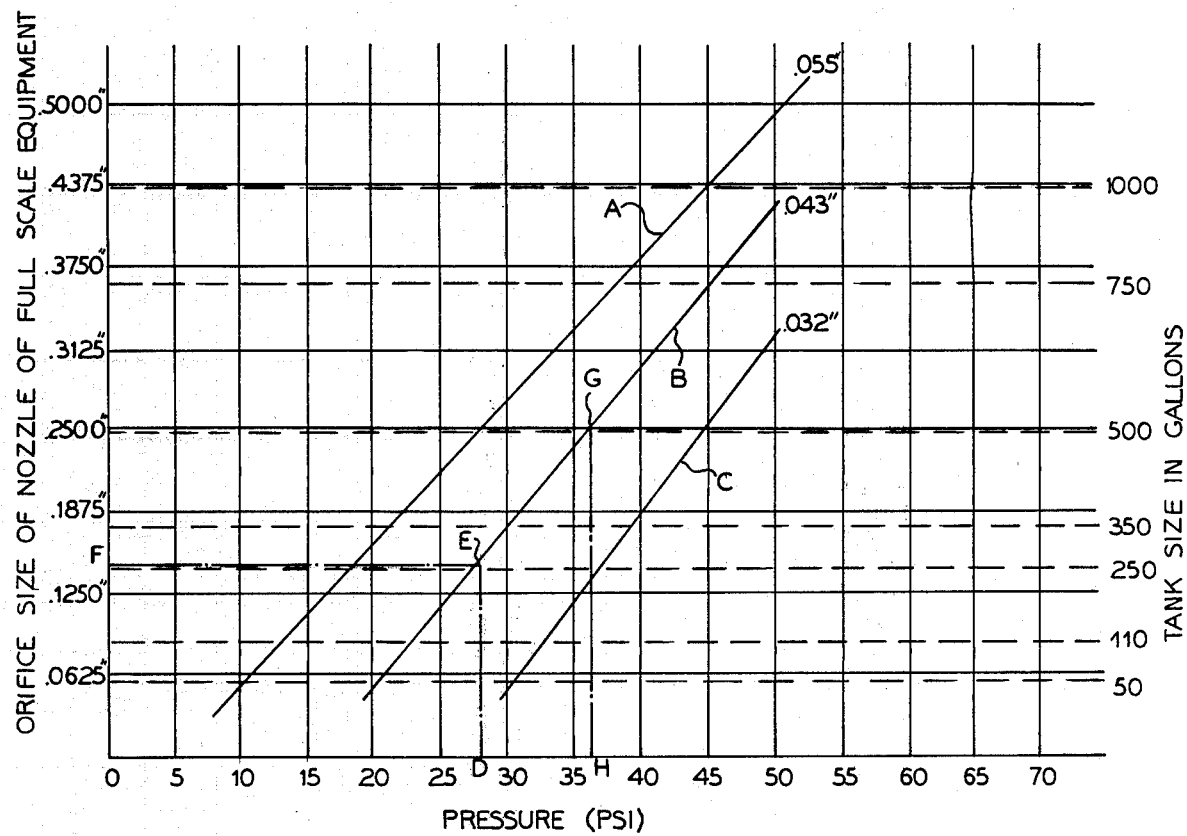
FIG. 13

EVALUATING SPRAYABILITY

BACKGROUND OF THE INVENTION

The field of this invention relates to testing apparatus and methods for evaluating sprayable water based compositions.

In recent years particularly as a result of the impact of the energy crisis, there has been a desire to apply in a single field pass a high concentration of sprayable solids or a mixture of different sprayable active agents so as to accomplish in single spraying operation a maximum amount of sprayed material application with a minimum consumption of energy.

Examples of composition which are sprayed at commercial rates include fertilizers, pesticides, herbicides, fungicides, and like biocides. As sprayed, a given formulation can be in the form of a suspension of solids in water (such as a colloidal suspension), and emulsion of oil or oil-like droplets suspended in a continuous aqueous phase, an aqueous solution, a mixture thereof, or the like. A large number of manufacturers of sprayable formulations exist and each manufacturer has his own manufacturing techniques, systems, and the like; not infrequently, a given manufacturer has trade secret information associated with his product or its manufacture. Commonly manufacturers of sprayable composition incorporate thereinto one or more surfactant additives to enhance the usability of the product. Commonly, sprayable compositions have come to be applied by farmers and professional spray applicators untrained in formulating chemical mixtures and these operators commonly endeavor to mix the product of one manufacturer with the product of another manufacturer in a single spray system; the spray applicator commonly does not know or even care about the exact chemical composition of the particular spray composition which he desires to utilize in his commercial operations. As a result of these variables, there has arisen in the art a need to evaluate a specific sprayable water based composition prior to its use in full scale commercial equipment. Such evaluations need to be carried out on a miniature scale and at low costs in a reliable and repeatable fashion. Unless such a preliminary evaluation is undertaken, the commercial sized batch of sprayable composition, in a given instance, may experience severe plugging of filter, or even the setting up of the entire batch in the reservoir, or like disaster so that an interruption in spraying is achieved to the great economic detriment of the user of the spray equipment.

Commercial spray equipment utilizes a very wide variety of nozzles, nozzle configurations, mixing conditions, inlet and outlet configurations, and the like. The equipment is not standardized with regard to sprayable mix recirculation requirements so that it is not possible to simply or easily determine conditions required in a given piece of equipment for minimum tank agitation for sprayability. Moreover, even a given water based sprayable composition can have different requirements for agitation from one piece of equipment to another because of inherent equipment operating variabilities.

The degree of chemical suspendability is no standardized in the biocide formulation industry. The extent of suspendability of a given type of formulation can vary from one manufacturer to another. Typically it is not possible for a user to determine the extent of agitation needed in a particular piece of commercial equipment which is sufficient to maintain a given sprayable composition in a homogeneous state for spraying. Furthermore condition required for homogeneity in a given sprayable composition may not be sufficient to maintain another type of sprayable composition even incorporating the same active ingredients.

The addition of more than one biocide or other material to be sprayed to a sprayable water based composition in a spray tank can create substantial mixing and compatability problems. Although manufacturers attempt to recommend all combinations of a given biocide formulation sold by them which they consider to be compatible (including combinations of products with other biocide manufacturers) such listing characteristically appear to omit certain combinations, perhaps because the manufacturer believes that such combinations should be avoided by a user, or perhaps because a complete list would be to exhaustive to be practical in the exigencies of the market place. Nevertheless, the operators of spray application equipment can either deliberately or inadvertently endeavor to combine various mixtures, including incompatible biocide formulations, resulting in disruptions in operations to their own great time and money and labor loss.

A simple reliable system for testing and evaluating sprayable compositions whether alone or in combination with other such compositions is needed in the art. However, so far is known, there has not previously existed either apparatus or method technology suitable for such miniature scale sprayability evaluation of sprayable water based compositions. The term "aqueous" as used herein is generally synonomous with "water based."

BRIEF SUMMARY OF THE INVENTION

By the present invention, there is provided novel apparatus and methods for evaluating on a miniature scale the sprayability behavior of a specific sprayable water based composition prior to the time when such composition is to be utilized in selected full-scale spray apparatus.

In one aspect, the present invention provides test apparatus for duplicating on a miniature scale the behavior of commercial scale spray apparatus. In another aspect, the present invention provides processes for evaluating on a miniature scale the sprayability behavior of a specific sprayable water based composition For one example, the present invention provides a process for determining whether or not a given sprayable composition can be admixed in a reservoir using only fluidic agitation involving a specific combination of nozzle configuration and nozzle pressure (within the reservoir).

For another example, the present invention provides a process for evaluating whether or not a homogeneous sprayable composition can be maintained in a reservoir, using a recirculation mixing pressure which is less than the mixing recirculation pressure used to create the mixture.

For another example, the present invention provides a process for determining how much of a given material (such as a surfactant or emulsifier) must be added to a water based composition which is being subject to mixing agitation using incremental recirculation in order to achieve a sprayable consistency, such as homogeneity.

A principle object of the present invention is to provide a system for evaluating on a miniature scale the sprayablility of various water based compositions.

Various additional features, advantages, aims, purposes, alternatives, and the like will be apparent to those skilled in the art from the teachings of the present specification taken with the accompanying drawings.

BRIEF DESCRIPTION OF THE DRAWINGS

In the drawings:

FIG. 3 is a schematic diagram of the system shown in FIG. 1;

FIG. 4 is a view similar to FIG. 3 but showing in schematic diagramatic form an alternative embodiment of the system of the present invention;

FIG. 5 shows an alternate arrangement for output of fluid from the reservoir in the system of FIGS. 1-3;

FIG. 6 is an enlarged fragmentary cross-sectional view taken generally along the line VI—VI of FIG. 5;

FIG. 7 is a view similar to FIG. 5 but showing an alternate arrangement for the orifice assembly;

FIG. 8 is a view similar to FIG. 5 but showing a further alternate assembly for the input orifice and the output orifice;

FIG. 9 is a view along the line VIIC—VIIC of FIG. 8;

FIG. 10 illustrates one embodiment of an alternative filter assembly for use in the spray system shown in FIGS 1-3; and FIG. 11 illustrates one embodient of an incremental feed arrangement for systematically charging into the reservoir of the system shown in FIGS. 1-3 a measured concentration of at a controlled feed rate of a surfactant or the like.

FIG. 12 shows a plot illustrating the relationship between pressure and extent of mixing for a sprayable system being tested in accordance with the teachings of the present invention; and FIG. 13 is a plot illustrating the manner in which test information derived from the plot of FIG. 12 may be used to select the nozzle size employable in a commercial spraying apparatus using the teachings of the present invention.

DETAILED DESCRIPTION

Referring to FIGS. 1–3, there is seen a system of the invention herein designated in its entirety by the numeral 20. System 20 comprises a testing and evaluating apparatus for duplicating on a miniature scale the behavior of a commercial scale spray apparatus of a conventional type to permit study and evaluation of the behavior of a specific sprayable composition under controlled conditions. The system 20 incorporates a pump 21 which may be of the centrifugal type (presently preferred). The pump 21 is characterized further by having a generally uniformed volumetric output of fluid at a predetermined fluid output pressure. The pump 21 has an input orifice 22 and an output orifice 23.

Pump 21 is driven directly by a variable drive means here illustrated as electric motor 25 (presently preferred), the motor 25 being adapted to be driven at variable speeds through use of a variable resistor 26 placed across leads 27 in the usual way (as shown). Varying the speed of motor 25 thus varies the volumetric output of fluid from pump 21.

System 20 further includes a reservoir 28 which in the embodiment shown has the configuration of an elongated cylinder which has fluid type circumferentially extending side walls 29 which are engaged with flattened end walls 30 (paired). Each such end wall 30 can be engaged with a side wall 31 by gluing or threadable engagement (as shown) using, for example, a spanner wrench inserted into receiving apertures 32. The reservoir 28 is supported in a clamped configuration by means of brackets (paired) 33. Each bracket comprises a base 34 which is engaged with a mating clamping cap 35 by means of screw means 37, as shown, for example. Each mounting bracket 33 is secured to the base plate 38 by screw means or the like (not detailed).

Motor 25 is associated with a mounting member 39 to which the pump 21 is bolted by means of nut and bolt assemblies 40. The motor 25 is mounted to base 38 by a mounting pad 41 by nut and bolt assemblies (not detailed by convention). Any convenient means, as those skilled in the art will appreciate, can be used to associate the pump 21 with the motor 25 and to mount such members in fixed relationship to the base 38.

The reservoir 28 is provided with an input orifice 42 and an output orifice 43. In the embodiment shown, the input orifice 42 is oriented in a gravitationally upper position in the side wall 29 while the output orifice 43 is located in the interior gravitational bottom of reservoir 28.

System 20 is further provided with a filter assembly 45 which may be of conventional construction for separating particulate material over a predetermined maximum particle size from a fluid circulated therethrough. In the embodiment shown, the filter assembly 45 is comprised of a housing 46 of metal, or the like, which has centrally disposed therein a cylindrical filter screen 47 which is adapted to be centrally disposed within the housing 46 being maintained in a clamped engagement therewith through the end plug 48. Fluid to be filtered is input into the filter assembly 45 through the input orifice 49 and is moved via channel 50 towards the elongated hollow central portion of the screen 47, as shown. Particles in fluid are caught in the interior of the filter 47 as the fluid moves through the screen 47 to be conveyed within the filter assembly 45 via channel 51 towards and through the output orifice 52.

A nozzle 53 is connected to elbow coupler 54 when the system 20 is in an operating configuration for testing purposes.

The system 20 is provided with a first tube 55 which interconnects the pump 21 with an orifice assembly 56 located in the gravitationally bottom interior portion of the reservoir 28. Thus, the tube 55 extends through the aperture 42 and terminates in functional association with orifice assembly 56. The orifice assembly 56 includes a nozzle 57 which is joined to a pipe fitting 58 that in turn is threadably associated with the terminal end of tube 55 within the reservoir 28. Conventional coupling and fitting arrangements can be utilized in all pipe connections employed in the practice of the present invention, as those skilled in the art will appreciate. It is presently preferred to employ stainless steel tube means, but, as suggested in the drawings, it is is preferred to have the reservoir 28 constructed of a transparent plastic material, such as polymethyl methacrylate, or the like, so as to permit visual or optical device observations, measurements, or the like, to be made through the walls of the reservoir 28.

A second tube 60 interconnects the outlet 61 of the reservoir 28 with the inlet orifice 49 of the filter 45.

A third tube 62 interconnects the output 52 of filter 45 with the input orifice 22 of pump 21.

Figure 1:
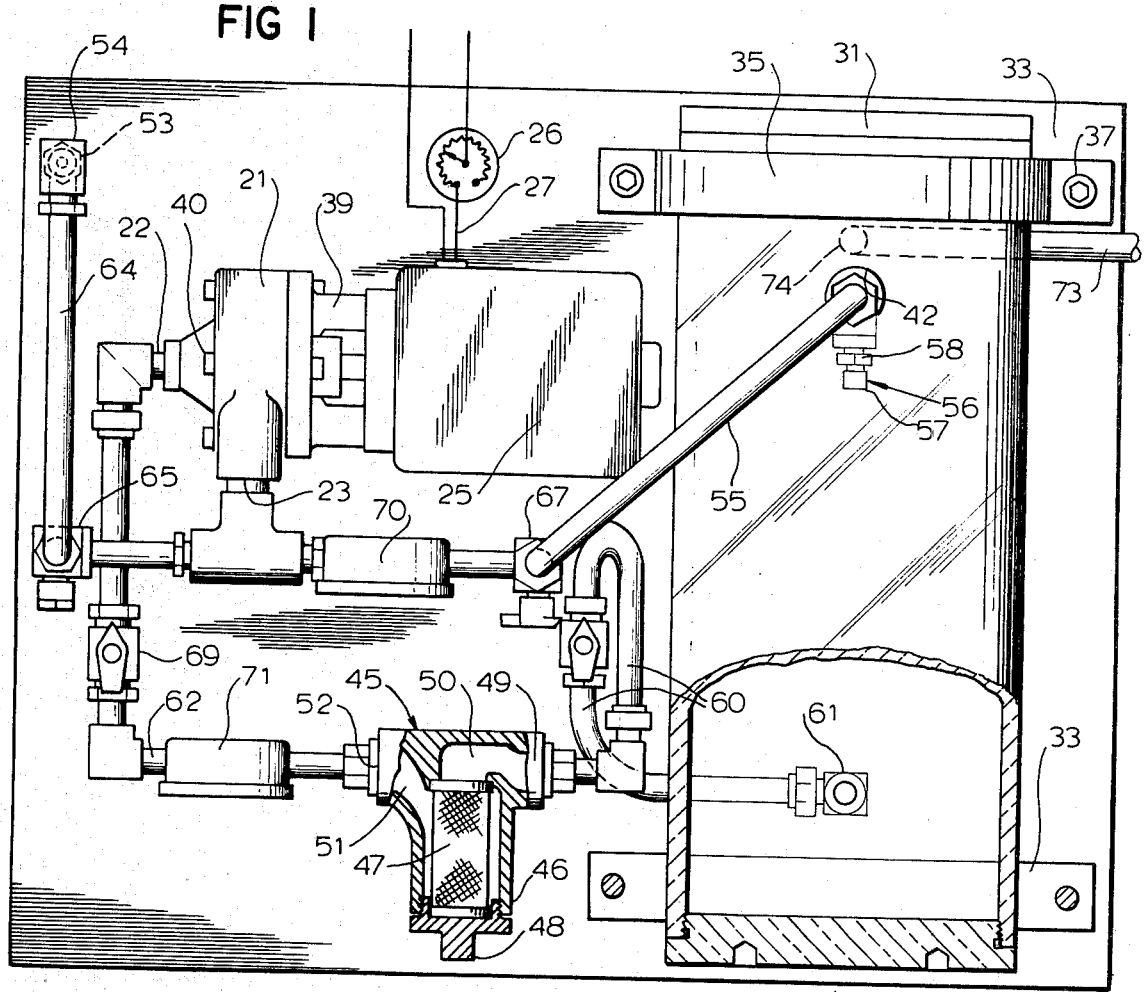
FIG. 1 is a plan view of one embodiment of a test system of the present invention.

A fourth tube 64 interconnects a T-fitting 63 in tube 55, the T-fitting 63 in the embodiment shown can be located adjacent the output orifice 23 of pump 21.

A first valve 65, preferably a ball valve, is located in the fourth tube 64 for controlling flow through such fourth tube 64.

A second valve 67 is located in the first tube 55 between the T-fitting 63 and the orifice assembly 56 for regulating flow through the first tube 55. Valve 67 is in a normally open configuration but can be partially or fully closed to regulate pressure level and associated flow rate through line 55 during operation of pump 21.

Respective third and fourth valve means 68 and 69 are associated with the input and output orifices 49 and 52, respectively, of filter assembly 45. These valves 68 and 69 permit isolation, when desired, of filter assembly 45 from its associated respective second and third tubes 60 and 62.

For control and test purposes, system 20 is provided with instrumentation. Thus, a pressure gauge 70 is positioned in line 55 between T-fitting 63 and orifice assembly 56. This gauge indicates the pressure in which fluid discharged from pump 21 flows through tube 55 into reservoir 28. In addition, the vacuum gauge 71 is provided in tube 62 and gauge 71 serves to indicate, during system 20 operation, whether or not the filter 47 is experiencing plugging or partial entrapment of solid thereon, as will be explained below. Any convenient instrumentation may be employed.

While system 20 is herein illustrated with a single nozzle 53, as those skilled in the art will appreciate, two, three, or more nozzles can be interconnected with the tube 64 during a testing operational sequence using system 20. The number of nozzles utilized in any given procedure is variable depending upon the commercial size spraying equipment which the system 20 is intended to resemble in any given testing configuration.

Operational sequence of the system 20 is as follows: Conveniently, water or a liquid fertilizer is charged from an exterior source (not detailed) through tube 73 into the reservoir 28 through an interconnecting orifice 74. Volumetrically, the amount of water or liquid fertilizer charged is such as to bring the final liquid level in reservoir 28 up to some predetermined desired level. Next, the system 20 is conveniently checked for operation by briefly operating the pump 21 through turning motor 25 off and on by a switch means (not detailed). Initially, valve 65 is closed and valve 68 is open, as is valves 69 and 67. Thus, when pump 21 operates, fluid circulates through the reservoir 28 at a charging pressure determined by the pump 21 operting speed (in the case of the centrifugal pump illustrated). The speed of the pump 21 can be varied by means of the rheostat 26 within the limits of equipment capability. As those skilled in the art will appreciate, typical commercial pumps associated with commercial scale spray apparatus currently develop pressures in the range from about 20 to 60 pounds per square inch gauge (about 1.4 to 4.1 atmospheres). Consequently, in the present test apparatus, the pump 21 is chosen so as to have a similar capacity.

In reservoir 28 mixing of a system to be sprayed is accomplished through a combination of input pressure through orifice 56 in relation to the distance between the orifice 56 and the outlet 61 of reservoir 28.

Fo testing purposes, any composition which it is desired to spray in a water based medium (water based media being almost universally employed for commercial spray operations) can be introduced into the reservoir 28 with water contained therein. Typically, a sprayable system can be in the form of an aqueous solution, a suspension of solid particles dispersed in an aqueous medium (including colloidal dispersions), an aqueous emulsion (such as one wherein small drops of a non-aqueous liquid are dispersed in a water phase with the aid of emulsifiers), or the like. In a commercial spray apparatus, the sprayable aqueous composition is preferably maintained in a substantially uniform or homogeneous condition by means of the agitation developed in the reservoir thereof through recirculation. Typically, this agitation is produced by recirculating a minor portion of the reservoir contents under conditions such that the fedback sprayable composition is injected into the main body of the liquid system contained in the reservoir through one or more orifices under a pressure and a flow rate sufficient to keep the contents of the reservoir homogeneous until the time when increments of the liquid sprayable composition in the reservoir is removed therefrom through an orifice for spraying.

For system pressure in a commercial scale apparatus, typically a single pump is employed at the present time. Initially a composition to be sprayed is mixed and made homogeneous in the reservoir through recirculation, as indicated above. When homogeneity of a composition to be sprayed is deemed to have been achieved, then a valve arrangement in the commercial system is opened permitting such homogeneous sprayable composition to be applied through spray nozzles. When this valve system is opened, the pressure of the pump is divided between a pressure used for spraying and a pressure used for recirculating a fraction of the reservoir contents in order to continuously maintain the sprayable system in the sprayer reservoir in a homogeneous state. The system 20 of the present invention duplicates this type of arrangement. Thus, in the reservoir 28, through means of the pump 21, a composition for spraying is able to be mixed to produce homogeneity for spraying. When homogeneity in reservoir 28 has been achieved, the valve 65 is open and whereupon such sprayable composition in reservoir 28 exits through the outlet 61, passes through the filter 45 into the pump 21, and is discharged through the output 23. Within the T-fitting 63, the sprayable composition is divided and a part thereof flows through tube 55 back into the reservoir 28 while another part thereof is discharged into the tube 64 and out through the nozzle 53. When the valve 65 is opened, a drop of from about 2 to 7 pounds of pressure in line 55 is achieved, which pressure drop is comparable to that achieved in commercial spray units. Nevertheless, this pressure drop is not sufficient, in a commercial scale spray unit, assuming a sprayable composition, to permit the homogeneity of this composition to be altered. In other words, the pressure drop in system 20 is not sufficient to permit, for example, a homogeneous composition to separate during the course of a succeeding spraying operation.

In using the system 20 of this invention in a test spraying operation with the valve 65 open, which employing a transparent reservoir 28, a party doing testing and evaluation can observe whether or not, in, for example, the case of a suspension, the pressure drop through the opening of the valve 65 is so great as to permit the contents in the reservoir to experience a settling, which is obviously undesirable, since then the contents being sprayed from the nozzle 53 change with the passage of time and a uniform spray application from system 20 (or a commercial scale unit) is not then achieved. If the pressure in line 55 drops to the point where a settling in the reservoir 28 occurs, then the agitation in reservoir 28 for a constant pump 21 output can be increased by changing to a smaller orifice size so that flow of liquid through the line 55 is constricted. Pressure increase in line 55 can be metered through observation of the pressure gauge 70 and the resultant increase in escape velocity through the smaller orifice will produce increased agitation.

Of course, as those skilled in the art appreciate, increasing the pressure in line 55 also tends to reduce the flow rate of liquid through line 55. It is possible that, under certain conditions of operation, an increase in pressure in line 55 combined with a reduction in flow rate therethrough makes it impossible to maintain homogeneity in sprayable composition to be maintained with reservoir 28. When homogeneity in a sprayable composition in reservoir 28 cannot be maintained at a constant pump pressure (such as 30 PSI or 2.04 atmospheres) even when orifice alterations in recycle line 55 are used, then, for example, the sprayable composition cannot be used in a commercial spray apparatus without achieving a change in the composition being sprayed through an orifice, such as orifice 53, over the period of time when spray-out of composition from the commercial reservoir takes place.

Also, as those skilled in the art will appreciate, when particles collect in the filter 45 to a sufficient extent to cause a disruption of the flow through the line 62, by similar reasoning, the contents of the sprayable system in the reservoir 28 cannot be maintained in the desired homogeneous condition. The present apparatus permits one to observe the contents of a composition in a reservoir 28 and also to observe the pressure and the pressure effects upon such composition (using visual observations) of the reservoir 28 and of the pressure shown on the vacuum gauge 71. For example, when the vacuum gauge pressure drops from a condition of no load (as when mere water is circulated through the system) when a sprayable composition is being partially or fully recirculated (the latter situation being in existence when the valve 65 is closed), the plugging in the spray filter 45 has occured. As those skilled in the art will appreciate, a plugging of a composition being sprayed in a commercial scale system can result in a severe disruption of a spray operation, loss of time, money, etc. Sometimes the culprit is not particle size of the particulate materials involved, but the fact that these materials can tend to adhere to interior portions of the apparatus including the screen 47 of the filter 45. Use of system 20 can minimize and prevent such plugging disruptions in a commercial scale operation.

By using a system 20 of the present invention, a variety of specialized test procedures, it has been discovered, can be undertaken which permit one to evaluate a spray composition before the same is subjected to field use conditions, thereby avoiding the problems heretofore known in the art of spraying.

To introduce a supply of water or liquid fertilizer into the reservoir 28 a tube 73 is provided which interconnects with reservoir 28 at orifice 74 (which is located in a gravitationally bottom portion of the reservoir 28). For example, a measured amount of a liquid fertilizer concentrate can be introduced into the system through 73 after which such concentrate can be diluted through the addition of a measured amount of water into the reservoir 28 through line 73. Alternatively, such a concentrate or such water can be introduced through the orifice 42, if desired.

In place of outlet 61 of reservoir 28, one can employ a discharge tube 75 as shown, for example, in FIG. 5. Here the discharge tube 75 connects with the tube 60 at outlet 61. The discharge tube 75 has formed therein a plurality of openings 76. Through each individual opening 76 liquid can be withdrawn from the interior of reservoir 28 so that the discharge tube 75 serves as a collection means along a significant inside bottom interior portion of the reservoir 28. Each opening 76 is so positioned relative to the interior of the reservoir 28 that it opens angularly towards bottom portion of the reservoir 28 as shown by the illustrative angle theta in FIG. 6. The angle theta can be of the order of from about 20° to 35° off the horizontal taken through the axis of the tube 75. The junction of such skewed openings 76 is to provide turbulence within the reservoir 28 thereby to enhance mixing action therein along the inside bottom interior portion of the reservoir 28. The cross-sectional area of the tube arrangement in the region of outlet 61 is equal to the accumulated cross-sectional openings 76 so that a constant flow capability of fluid through the interior of reservoir 28 may be maintained. Thus, there is no change in the system shown in FIGS. 1–3, for example, compared to the modification shown in FIGS. 5 and 6, so far as flow rates through reservoir 28 are concerned.

Referring to FIG. 7, there is seen an embodiment wherein a reservoir 28″ is provided with an orifice 43″ which is provided with a drain line which can be substantially identical to that shown, for example, in FIG. 2. However, in this embodiment of FIG. 7 the tube 55″ interconnects with an elongated orifice assembly 92 which extends along the gravitationally bottom interior portion of the reservoir 28″. The elongated orifice assembly 92 has a tubular configuration and is provided with a plurality of longitudinally spaced small openings 93 which are positioned so as to open downwardly (relative to gravity) in the reservoir 28″. The jetting action produced by the openings 93 aid in dispersing uniformly a water based mixture in the reservoir 28″.

In FIG. 8, a combination of the system shown in FIG. 5 and the system shown in FIG. 7 is incorporated into a single reservoir 28‴. Here, the tube 55‴ interconnects with an elongated orifice assembly 92′ while the orifice 43‴ interconnects with a tube 75′ which is provided with openings 76″. The relationship between the tube 75′ and the elongated orifice assembly 92′ is shown in, for example, FIG. 9. Here, the openings 93′ in assembly 92′ are directed so that the angle phi at which such openings exit from assembly 92′ fall in an angle phi which extends from about +25 degrees to −45 degrees from the horizontal while the openings 76′ are directed downwardly so that the entire assembly coacts to enhance mixing action within a reservoir 28‴.

A preferred method is to have a sump the length of the reservoir and spray tube for recirculation, located directly above with the orifices 25°–35° off horizontal, etc.

In FIG. 10, there is shown an alternative embodiment for a filter assembly adapted for use in the system 20 shown generally in FIGS. 1–3, such alternative filter assembly being herein designated in its entirety by the numeral 95. Assembly 95 is comprised of a housing 97 of metal which has centrally disposed therein a cylindrical filter screen 97. Screen 97, in turn, is centrally disposed in a transparent plastic cup-shaped member 98 whose lip portions are threadably engaged with mating portions of the housing 96, a ring-shaped seal 99 being provided to achieve a fluid-tight engagement between cup 98 and housing 96. Opposing end portions of the screen 97 are provided with a sealing sleeve member 100 which at one end sealing engages with mating portions of housing 96 and which at the other end sealingly nests against the inside bottom wall of the cup 98. The housing 96 is threadably engaged with the lines 60' and 62' in a manner similar to that achieved for the filter assembly 45.

In operation, fluid charged into filter assembly 95 enters through line 60' into the channel 101 from which fluid is conducted around circumferentially outer portions of the screen 97. In the embodiment shown, the screen 97 is comprised in its circumferential portion of a stainless steel wire, or the like, such as a mesh construction, with the interstices between the wire mesh providing filter openings into the central hollow interior thereof. Thus, particles entering with fluid into the channel 101 are entrained upon circumferential outer surface portions of filter 97. A build-up of solid particles can occur in interior bottom portions of the cup 98 adjacent to the filter 97. In this arrangement, an operator of system 20 can observe a build-up of filtered particles in the filter assembly 95, and also an operator can observe the nature and character of such particles. For example, in the case of an emulsion composed of particles which have a "cottage cheese" type of appearance, an operator or observer can form a judgement concerning the origin and nature of these particles while evaluating a sprayable composition in a system 20. Liquid passing through the filter 97 into the central interior thereof exits from the filter assembly 95 through the channel 103 from which the liquid enters the tube 62'. The cup 98, as shown, is preferably adapted for simple, rapid engagement or disengagement with the housing 96 in order to facilitate test and evaluation procedures. Any convenient structure for the central filter arrangement can be employed in place of the screen 97, as those skilled in the art will appreciate. For example, a fluted conventional cellulosic filter may be substituted for a wire screen, if desired.

Figure 2:
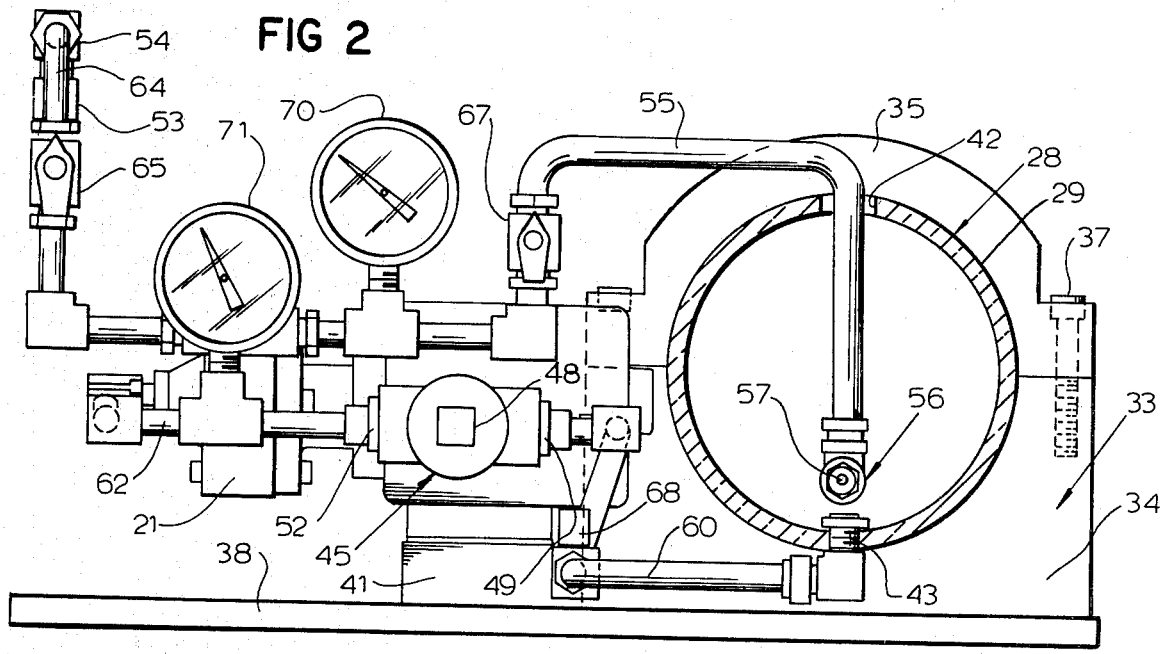
FIG. 2 is a side elevational view of the system shown in FIG. 1, some parts thereof being shown in section.

Referring to FIG. 11, there is seen a charging subassembly for a reservoir 28, which charging assembly is designated in its entirety by the numeral 105. The charging assembly 105 is conveniently integrated with, and supported by, a clamping cap 106 which also functions in a manner similar to the clamping cap 35 in the embodiment shown in FIGS. 1–3. An opening 107 is provided in side wall 29 of reservoir 28 which is sealingly engaged with a channel 109, the seal being achieved by means of an O-ring 101, or the like, as desired.

Charging mechanism 105 is provided with a reservoir 111 which is here in the form of a funnel having a graduated stem 112. The funnel portion of the reservoir 111 can hold a liquid, such as a surfactant or emulsifier concentrate which is to be evaluated in the operation of system 20 in combination with a sprayable composition. The base 113 of the stem 112 is tapered and adapted to be matingly received in a tapered orifice formed in cap 106 for rapid connection and disassociation of the reservoir 111 from the cap 106 (as for cleaning, or the like). For example, when the system 20 is to be made portable and housed in a case (not detailed), it is desirable to have a reservoir 111 adapted for disassociation from cap 106 (for transport and storage purposes). Adjacent base 113 and integrally formed into the stem 112 is a stopcock assembly which is herein designated in its entirety by the numeral 116. Stopcock assembly 116 can be of conventional construction so that, for example, the plug 117 thereof can be turned through 90° by an operator to to achieve open and closed positions for opening and closing a fluid passageway 117a within the plug 117, thereby to provide a simple and reliable valve for the reservoir 111 which can be disassembled readily for cleaning and the like.

In operation, an initial calibration operation is generally contemplated for use of the charging mechanism 105. In such a calibration operation, the stem 112 is filled to some desired level to provide a fluid therein whose level can be read from the calibration provided therein, with the reservoir 111 engaged with the cap 106.

A syncro motor 118, or the like, is mounted on a bracket 119 which is clamped to the cap 106 by bolts 120. The drive shaft 121 of motor 118 is provided with a crank arm 122 which is keyed to the shaft 121 for rotational movements therewith (the keying not being detailed). A rocker arm 123 is provided which is pivotably associated at its base end with the bracket 119 by means of a pin 124 which is received through a flange in the bracket 119. The rocker arm 123 is interconnected with crank arm 122 by means of a link 125. The link 125 is preferably longitudinally extensible or retractable by means of a screw adjustment 126 which is of the conventional sort well known to those skilled in the art. In order to control the throw of rocker arm 123, a longitudinally extending slot 127 is provided in an upper portion thereof (relative to pin 124). This slot 127 provides an infinitely adjustable region for connecting the link 125 thereto by means of a nut and bolt assembly 128 to provide further adjustments in motion of the rocker arm 123, a longitudinally extending slot 129 is provided in crank arm 123, a longitudinally extending slot 129 is provided in crank arm 122 through which a nut and bolt assembly 130 can be adjustably engaged in order to associate the link 125 with the crank arm 122. The slot 129 permits one to adjust the rotational diameter associated with the movement of link 125, as those skilled in the art will appreciate.

Intermediate between pivot pin 124 and slot 127 is a pivot pin 131 which extends through rocker arm 123. Arm 123 is pivotably engaged with one end of rod 132. The opposed end of rod 132 is engaged with a piston 134. Thus rotational movements of the shaft 121 are converted into the reciprocal movements associated with the piston 134. Piston 134 is provided with annular sealing O-ring members 135 which are adapted to make a sealing engagement with the adjacent walls of the cylinder 137 which matingly engage the O-ring members 135 and wherein the piston 134 reciprocates during operation of the motor 118. The head 138 of cylinder 137 is provided with a pair of spaced apertures 139 and 140, respectively. Each aperture 138 and 139 leads to a check valve assembly 141 and 142, respectively. Check valve 141 and 142 are each of the simple ball and spring arrangement for reasons of convenience, simplicity and reliability, but, as those skilled in the art will appreciate, any convenient check valve arrangement can be employed. The check valve assembly 141 is adapted for one way flow of liquid or fluid therethrough from the base of stem 112 through channel 143 into the interior of the cylinder 137, while the check valve assembly 142 is adapted for one way passage of fluid therethrough from the interior of cylinder 137 into the channel 109.

Thus, when the stopcock assembly 116 is open so that liquid from reservoir 111 or from stem 112 can pass therethrough, and when the piston 134 is being driven by motor 118, liquid is moved from the stem 112 into the interior of the reservoir 28 at a constant rate with respect to time, the exact rate of metering from stem 112 being selected by an operator. The speed of rotation of shaft 121 can be preselected by choice of motor 118, and, in addition, the stroke of the piston 134 can be adjusted, as those skilled in the art will readily appreciate.

By means of the charging mechanism 105, an operator of system 20 can meter into the interior of the reservoir 28 a chosen material from reservoir 111 at a constant rate.

As a consequence of such a capacity to feed from reservoir 111, an operator can select a predetermined composition for example, of water and finely divided solids. With the system 20 operating in its mixture mode so as to achieve a predetermined level of mixing within the reservoir 28, one can meter into the reservoir 28 at a constant rate material from reservoir 111 until, for example, some predetermined effect is achieved, such as, for example, a condition of true homogeneity. By selecting a rate of material addition from reservoir 111 which is compatible with the rate of mixing chosen for a given operation of system 20 mixing action in reservoir 29, an observer can visually determine how much, material (e.g. surfactant liquid or the like) must be charged from the reservoir 111 into the reservoir 28 before a homogeneous suspension is obtained in reservoir 28 through material addition. The procedure involves initially starting the mixing action in reservoir 28 until maximum mixing is achieved with no addition of material from reservoir 111. Thereafter, material addition from reservoir 111 is commenced, and, as soon as homogeneity is achieved, reservoir 111 is cut-off from reservoir 28 either by closing the stopcock 116 or by stopping motor 118 as the operator desires.

In order to determine the total amount or volume of material fed into reservoir 28 from reservoir 111, a piston stroke counter assembly 144 can be employed. In the embodiment shown, the stroke counter employs a micro-switch 143 which is tripped once during each revolution of the crank arm 122, each tripp signifying that the piston 135 has completed one complete stroke. Ny calibrating, for example, the stroke counter 144 to read directly the volume of liquid passed through the cylinder 137 during each stroke of the piston 134, an exact indication of the total volume of material needed from reservoir 111 can be obtained, assuming an appropriate preliminary calibration is carried out using the graduated stem of the reservoir 111, as indicated above.

A preferred method is to have a sump the length of the reservoir and a spray tube for recirculation, located directly above with the orifices 25°–35° off horizontal, etc.

Referring to FIG. 4, there is seen a modified system of this invention herein designated in its entirety by the numeral 80. System 89 is similar to system 20 except that system 80 employs, in place of the motor 25 pump 21 assembly, two pump assemblies 81 an 82, respectively. Pump 81 is driven by motor 83 while pump 82 is driven by motor 84. The combination of pump assemblies 81 and 83 plus respective motors 82 and 84, is comparable to the motor 25 pump 21 assembly of system 20. Thus, instead of having one pump which splits the flow between spray head and mixing nozzle (in reservoir 28), the present system 80 uses the pump 82 to provide pressure for spray head 85 while the pump 81 is employed to maintain pressure in line 86 for independently pressurizing nozzle 87 in reservoir 28′ for maintaining a desired mixing capacity within the reservoir 28′. In general, components in system 80 which are similar to those in system 20 are similarly numbered but with the addition of prime marks thereto for reasons of convenience and simplicity. By using a separate pump 81 to maintain pressure in line 86, one can achieve a constant pressure in the reservoir 28 even after the spray head 85 is rendered operative through activation of the pump 82. Observe that the tube 62′ interconnects with the tube 91 in system 80. Tube 91 is an intake supply line to each of the respective pumps 81 and 82 from reservoir 28′. The arrangement shown in system 80 permits a minimal pressure disturbance between tube 86 and tube 89 which is desirable for accurate test and evaluation purposes.

In a commercial sizes sprayer, the art conventionally employs a single pump and drive for reasons of cost and simplicity which makes it difficult to independently evaluate mixing pressure changes relative spraying pressures.

In one mode of practicing the test technology of the present invention, one practices a process for evaluating on a miniature scale the sprayability behavior of a specific sprayable aqueous composition. To practice this process, in a first step using, for example, the system 20 of the present invention, one mixes the non-aqueous components of at least one sprayable composition (or composition whose sprayability is to be tested) with a desired quantity of water or liquid fertilizer in an elongated reservoir. The mixing in such reservoir is achieved by the steps of removing a minor portion of the resulting mixture from a first gravitationally bottom region of the reservoir and then injecting such minor portions under pressure through a nozzle member positioned in a second gravitationally bottom region of the reservoir. This second region is in longitudinally spaced relationship to the first region in said reservoir. In this mixing, the reservoir has an internal length ranging from about 10 to 50 centimeters and an internal volume ranging from about 1 to 6 liters. Also, in such mixing, the nozzle member in the reservoir has a cross-sectional area in its region of maximum constriction which is less than about 0.5 square centimeters.

As can be seen from the preceding description of system 20, various arrangements within the reservoir can be employed with respect to the location of one or more nozzle members and the region longitudinally spaced therefrom wherein such minor portions of mixture are drawn-out from a reservoir. Any convenient arrangement desired for test purposes in practicing the evaluation technology of this invention can be employed as those skilled in the art will appreciate.

While the mixing is proceeding, as indicated above, one determines the extent of mixing occuring in the reservoir for a given nozzle member cross-sectional area and for at least one selected nozzle pressure. Suitable nozzle pressures range from about 20 to 40 pounds per square inch gauge (about 1.4 to 2.7 atmospheres) since pressures in this range are commonly associated with commercial spray apparatus units. The extent of mixing, in accordance with the present invention, is determined after a predetermined mixing time interval, such as 10 minutes, 15 minutes, or the like.

Thereafter, one correlates the extent of mixing so determined with the extent of mixing achieved in a selected full-scale mixing apparatus (such as a commercially available spray apparatus which is to be used for field spray use) wherein the comparable reservoir nozzle member has a cross-sectional area (which is known) that is greater than about 0.5 square centimeters (about 0.077 square inches) and wherein the comparable reservoir member has an internal length greater than about 50 centimeters (about 20 inches) and an internal volume greater than about 6 liters (about 1.6 gallons).

As those skilled in the art will appreciate from the preceding description, by determining the extent of mixing occurring in the reservoir for at least one selected nozzle pressure, one can determine whether or not the sprayable composition under test can be mixed in the selected full-scale mixing apparatus, especially after the initial start-up phase in such apparatus when a spraying operation is underway and the pressure is reduced during mixing because of the fact that the spray apparatus is using a portion of its pressurizing capability to pump out the sprayable composition in a spraying operation. However, for test purposes, it has been found that the use of such a single nozzle pressure in the test apparatus may not be sufficient to give a good indication of the minimum nozzle pressure in the reservoir which is sufficient to produce substantial homogeneity in the resulting so mixed mixture. In order to determine this sufficient nozzle pressure for homogeneity of mixture, the extent of mixing step is repeated a plurality of times, and each respective repeat is conducted at a different constant nozzle pressure within the reservoir. At the end of the mixing time interval, the nozzle pressure and the extent of mixing are conveniently noted. From the data collected, a nozzle pressure which is sufficient to produce substantial homogeneity in the resulting so-mixed mixture is readily determined.

For example, referring to FIG. 12, for a given test nozzle (having a fixed orifice cross-sectional area), one can determine the extent of mixing for increasing nozzle pressures to produce a plot such as illustrated in FIG. 12. Since, at the present time, the state of the art provides no quantatative means for determining the extent of mixing in a reservoir, it has been found convenient to perform visual observations of the fluid in a reservoir during a test mixing operation.

FIG. 12 represents nominal pressures for given orifice sizes on the recirculation line in the system 20 reservoir 28. The "x" axis is line pressure (psig) in the system 20 recirculation line. The "y" axis is divided into four equidistant points or tick marks representing various degrees of mixing in such system 20 reservoir. Tick mark #1 is visually observed or identified in the system 20 reservoir as motionless particles resting on the entire bottom. Tick mark #2 is visually observed or identified in the system 20 reservoir as eddy currents with pockets of motionless particles. Tick mark #3 is visually observed or identified in the system 20 reservoir as strong eddy currents with pockets of particles in slow movement about the bottom. Tick mark #4 is visually observed or identified as particles in constant motion evenly distributed throughout the solution in the reservoir of the system 20. As can be seen from FIG. 13, each size orifice has a minimum pressure associated with it to provide nominal agitation. A given parametric curve "A", "B" or "C" of FIG. 12 should be chosen so that this minimum pressure is obtained in any given situation. In a given test procedure, a pressure greater than that needed to obtain homogeneity may be achieved in a given test procedure, however, by interpolation of test results an estimate can be obtained of the value needed to obtain true homogeneity of the testing composition. Because of the fact that each individual sprayable system will have a curve which is unique to that system it is not possible to show in, for example, a figure such as the plot of FIG. 7 the generalized relationship between homogeneity and orifice pressure. Each sprayable system, based on information now available, appears to have a different family of curves for the relationship between pressure and extent of mixing relevant to particular test orifice sizes. Only experimentally, it now appears, can such a family of curves be developed for a given sprayable composition, a fact which emphasizes the importance of the present invention since it provides a true and scientific manner for evaluating on a miniature scale the sprayability behavior of a specific composition whose sprayability is to be determined. To aid in quantifying the sprayability of a composition each point on the ordinate of a plot such as FIG. 12 can be determined by a plurality of factors, such as estimated degree of uniformity of the mixture, filterability of the mixture, foaming characteristics of the mixture, affect on the transmittance of light through the reservoir (particularly with increasing pressures) and the like.

After one thus determines, for a given specific sprayable composition the nozzle pressure (for a given nozzle) which is sufficient to produce substantial homogeneity in the resulting so mixed mixture, then that sufficient pressure for such given nozzle member is correlated with the same corresponding pressure in a full-scale spray apparatus and with an equivalent larger sized nozzle member needed in such full-scale spray apparatus to produce a mixture in such full-scale apparatus which has the desired substantially complete homogeneity.

As is shown in FIG. 13, the degree of agitation is dependent on reservoir size and flow rate. Also, the larger an orifice, the greater the flow rate therethrough at a given pressure. Restated, less pressure is needed in a larger orifice to obtain the same flow rate as a smaller orifice. Therefore, the pressure times the orifice area is a function of flow rate and agitiation is a function of flow rate and reservoir volume. This means that pressure and orifice size are related to the degree of agitation. As seen from FIG. 13, in the present mode of practicing this invention, minimum orifice size for a given volume of reservoir of a commercial size tractor sprayer is noted by a dashed line. The "x" axis (abscissa) is line pressure and the "y" (ordinate) is the orifice size in inches for full scale spray equipment. The lines designated "A", "B", and "C" represent parametric curves or equations for three nozzle sizes in the system 20 reservoir.

In one mode of practicing this invention, the reservoir capacity of a chosen full scale spray system is determined as is the orifice size in the agitation head of its reservoir. The orifice size of the agitation head should be at least equal to or larger in size than that designated on FIG. 13. When this is not true, then the agitation head in the chosen full scale equipment is changed to give one an orifice of at least such minimum size or larger. One locates the orifice size to be used in such full scale equipment on the "y" axis of FIG. 13. From there, one draws a line parallel to the "x" axis intersecting the prametric curves "A", "B" or "C". At the point of intersection of curve "A", "B" or "C" one drops a perpendicular down to the "x" axis. The point of intersection on the "x" axis designates the pressure at which one should run the recirculation line in system 20 for nominal agitation. The point of intersection of parametric curve "A", "B" or "C" designates the orifice size, and the corresponding perpendicular intersection of the "x" axis indicates the pressure to be used in the system 20 to simulate the operation of such chosen full scale equipment.

For example, referring to FIG. 17, from the information developed in a plot such as shown in FIG. 12 one can select for the test orifice size the parametric shown in FIG. 13 corresponding to that orifice size. For example, for a test orifice cross-section area of 0.043 inch (corresponding to 0.813 square centimeters) one moves along the parametric curve to Point E which represents the line pressure desired, such as Point D, 28 pounds per square inch (corresponding to 1.90 atmospheres) gauge. Thereafter with this information one then reads horizontally from the parametric curve over to the ordinate Point F and determines the nozzle size which should be used in the reservoir of the commercial scale equipment in order to obtain homogeneity. If in fact the nozzle in the commercial scale equipment is larger than the size shown from such data than no change presumably needs to be made, provided the increased pressure for the nozzle size in the commercial tank projected back to the same parametric curve (but at a higher point therealong) results in a useable mixture when such test nozzle has been experimentally evaluated at high line pressure and found to produce acceptable homogeneity. For example, with a commercial nozzle size of 0.25 inch diameter (corresponding to 0.64 centimeters) it is found that the intercept with the test nozzle occurs at Point G along the parametric curve for a test nozzle orifice of this size. Projecting this value downwards, it is found that a line pressure of 36 PSIG (2.45 atmospheres) Point H results which can then be generated in the system 20 (or equivalent) in order to verify that the higher or larger size nozzle pressure in the commercial equipment is useable without changing same.

In determining the extent of mixing occuring in a reservoir using a system 20, as those skilled in the art will appreciate, since most contemporary full-scale spray apparatus units are operated at pressures ranging from about 20 to 40 pounds per square inch gauge (about 1.4 to 2.7 atmospheres) the mixing evaluation will typically be conducted with pressures in this size range, although larger and smaller pressure may be desirable, of course, for test and evaluation purposes. In a preferred mode of evaluating mixability, the sufficient pressure necessary for production of substantially complete homogeneity in a mixture is determined by comparing each individual repeat nozzle pressure measurement to the extent of mixture mixing at such pressure at the end of the mixing time interval and then thereafter the results are interpolated so as to estimate the pressure required to obtain the desired substantially complete homogeneity. The extent of mixin at each individually measured nozzle pressure is determined prefereably by optical inspection at the present time of the interior of the liquid phase of the system in the reservoir.

In one particularly convenient procedure, the repeating of nozzle pressure measurements in the reservoir is carried out by starting with a predetermined upper pressure within the predetermined pressure range involved. Thereafter one gradually decreases the chosen upper pressure incrementally to respective lower pressures at a time rate of decrease ranging from about 2 to 10 pounds per square inch gauge (about 0.14 to 0.68 atmospheres) per minute until a pressure is reached where the liquid phase of the mixture in the reservoir optically appears to be substantially homogeneous. By following this procedure, a relatively rapid determination of nozzle size and pressure value needed for substantially complete homogeneity in a given mixture can be determined in a simple manner particularly by a trained operator of the system 20.

In another mode of practicing the process technology of the present invention, there is provided a process for evaluating on a miniature scale the sprayability behavoir of a specific sprayable water based composition from a selected full-scale spray apparatus. This process of evaluating commences with the assumption that a substantially completely homogeneous water based sprayable composition can be maintained in a reservoir through the action of incremental recycling of water based sprayable composition. The apparatus employed is a system 20, for example. Thus, this process commences by continuously removing incremental portions of a substantially completely homogeneous, water based sprayable composition from one region inside a reservoir.

Concurrently, one continuously pressurizes one fraction of such so removed incremental portions and injects such so pressurized one fraction continuously through a nozzle member located in the reservoir at a second region inside thereof. This second region is in spaced relationship to the aforeindicated one region. The relationship between the pressure and orifice of the nozzle member in the reservoir is such that there is produced in such reservoir a mixing action in the liquid phase of the aqueous sprayable composition. The pressure employed in such pressurizing is a value which is initially assumed to be at least sufficient to maintain the liquid phase contents of the reservoir in a substantially completely homogeneous condition.

Concurrently one also continuously pressurizes the remaining fraction of such so removed incremental portions and ejects such so pressurized remaining fraction through a spray head.

One collects at least one first sample of the water based composition so ejected through the spray head at a predetermined starting time. Then, at a predetermined end time following such starting time one collects at least one second sample of such water based sprayable composition so ejected through such spray head. One measures the degree of settling associated with such first sample after a measured time interval and one measures the degree of settling associated with such second sample after a measured time interval. Finally, one compares the first so measured degree of settling to the second so measured degree of settling to generate a ratio.

When this ratio has a value of unity, the initially assumed pressure used for pressurizing the one fraction recycled through the nozzle member is adequate to maintain the water based sprayable composition in a substantially completely homoeneous condition. However, when the value of this ratio is not unity (the value will be above or below unity depending upon which measured degree of settling is made the numerator and which the denominator), a further measurement is made. This further measurement involves a determination of the amount of increased pressure required in pressurizing the one fraction being recycled to the reservoir over the initially assumed value to cause the ratio to return to a value of unity and/or may induce the reduction in orifice size in the reservoir.

Since, in accordance with the present invention, the system 20 uses operating pressures which are comparable to those associated with a full scale spray apparatus, a measurement of the amount of such increased pressure required when the ratio is other than unity provides the information needed to increase the recycle pressure employed in the operation of a full-scale (commercial sized) spray apparatus. As those skilled in the art will appreciate, once the information is obtained as to the amount of incrementally added pressure needed in order to maintain homogeneity is known, it is a relatively simple matter to increase the line pressure on recycle to the reservoir to obtain the needed value. Such an adjustment can be made by either increasing the pump operating speed (in the case of a centrifugal pump) or by using an orifice with a smaller cross-section in the reservoir recirculation time, which causes the line pressure to increase. Up to a certain point, which is a point that is changeable from one machine to another, and sometimes for one spraying composition to another in the same machine, the associated drop in flow rate associated with a constriction of line pressure is not initially such as to disrupt machine operation. However, with increasing restriction of the recycle line there does result a point where the flow rate is so decreased that it is not sufficient, even with increased line pressure, to maintain the sprayable aqueous composition in its desired state of substantially complete homogeneity.

The apparatus and methods of this invention can be used for evaluating non-aqueous liquid systems such as systems where water is replaced by aromatic or aliphatic hydrocarbon solvents.

The present system 20 or system 80 through replacement of the spray nozzle, in each system, can be used for a dynamic fluid reactor, such as a reactor adapted for use in emulsion polymerization and the like wherein recirculation agitation provides a useful means for achieving reaction between homogeneously admixed components. Reactions may be carried out batch-wise or continuously using the systems of this invention with product being removed into a holding tank (not detailed) via a line such as line 64 in system 20, as those skilled in the art will appreciate. Alternatively, effluent from a reactor, such as reservoir 28, may be removed through line 73, if desired.

The apparatus of the present invention provides a convenient and efficient system for the systematic evaluation of sprayable systems on a small spraying scale (assuming adquate mixing and like variables are satisfactorily achieved through the operation of this equipment). An extension tube or flexible hose, or the like, can be used to position the spray nozzle 53 remotely from the vicinity of a system 20 or a system 80. In such a configuration, the system 20 or system 80 can be used to spray the interior of green houses, test plots, or the like.

If desired, the spray head associated with a system 20 or a system 80 can be positioned within a shaped housing, such as a hemisphere or the like, in order to conduct systematic testing and evaluation of spray patterns, nozzles and the like on a laboratory scale. Observe that a system 20 or a system 80 can be utilized with commercial sized spray nozzles for the dispensing of sprayable formulation prepared in a reservoir 28 or the like.

In a preferred mode of using a system, such as system 20, of the present invention for evaluating sprayable composition, one evaluates the quantity of additivive material necessary to achieve homogeneity of a specific starting sprayable composition. The evaluation method here utilized comprises in a first step the continuance mixing of non-aqueous components of the sprayable composition with a desired quantity of water in a reservoir 28. The mixing is achieved by the recirculation under pressure of incremental portion of fluid in the reservoir. The nozzle member in the reservoir has a cross-sectional area in its region of maximum constriction which is less than about 0.5 square centimeters.

While such mixing in the reservoir 28 is preceding, one adds to the reservoir a predetermined material at a predetermined rate of addition. A suitable such predetermined material can comprise, for example, a surfactant or emulsifier (presently preferred types of material). The rate of such addition is such that the material so added becomes substantially completely mixed with the mixture of sprayable composition in the reservoir within a total time interval which is not greater than about the time which is necessary to achieve a cumulative removal of resulting mixture from the reservoir, equal to the total volume of the mixture therein.

While such mixing and adding are progressing, one senses the extent of homogeneity of the fluid in the reservoir, such fluid comprising the combination of resulting mixture and added material blended therewith. One stops adding the added material while continuing the mixing when such sensing shows that the combination of the resulting mixture and the added material in the reservoir has achieved a predetermined level of uniformity.

Preferably such level of uniformity comprises a substantially homogeneous condition. Preferably the total volume of the resulting mixture in the reservoir is not more than about 6 liters with the reservoir size being not more than about 7 liters. Also, preferably the mixing is conducted at a turnover rate (that is the rate necessary to achieve one complete removal of mixture in the reservoir equal to the total volume of mixture in the reservoir) which is not greater than about 5 minutes.

The present invention is further illustrated by reference to the following examples. Those skilled in the art will appreciate that other and further embodiments are obvious and within the spirit and scope of this invention from the teachings of these present examples taken with the accompanying specification.

EMBODIMENTS

The present invention is further illustrated by reference to the following Examples. Those skilled in the art will appreciate that other and further embodiments are obvious and within the spirit and scope of this invention from the teachings of these present examples taken with the accompanying specification. CAUTION: Operation of spray nozzles produce a large volume of mist. Proper safety precaustions should be taken to protect operator. This should include gloves, safety glasses, respirator and protective clothing. Mist can be greatly reduced by allowing effluent to spray into a sink or large tank with one inch of water in the bottom, provided the spray pattern does not hit any of the sides of the tank. If spray patterns are not being tested, then a short piece of rubber tubing placed over the spray nozzle will still allow collecting of effluent and reduce mist.

EXAMPLE 1

General Procedure for One Operating Mode of Using a System 20

Setting Lab Sprayer

1. Select particular commercial scale spray machine
2. Determine ground speed of the tractor sprayer to be used.
3. Determine gallons per acre of water or liquid fertilizer to be applied.
4. Measure distance between nozzles of the tractor sprayer. Refer to Table I calibration chart. (See below.)
5. Find the ground speed in mph or feet per minute on the lefthand column, and the gallons per acre required across the top.
6. Obtain the calibration factor at the intersection of these two columns.
7. Multiply this factor by the distance in inches between nozzles on the spray boom. The answer obtained in step 6 is the ounces per minute one should catch from each nozzle to accurately spray the specific number of gallons per acre chosen.

Calibration Chart

| Miles per hour with full load | No. feet Traveled Per Min. | 20 gal/ AC | 25 gal/ AC | 30 gal/ AC | 35 gal/ AC | 40 gal/ AC |
|---|---|---|---|---|---|---|
| 2.0 | 176 | .86 | 1.06 | 1.29 | 1.50 | 1.72 |
| 2.5 | 220 | 1.07 | 1.34 | 1.62 | 1.88 | 2.14 |
| 3.0 | 264 | 1.28 | 1.61 | 1.93 | 2.26 | 2.57 |
| 3.5 | 308 | 1.50 | 1.88 | 2.25 | 2.63 | 3.01 |
| 4.0 | 352 | 1.71 | 2.14 | 2.57 | 3.00 | 3.43 |
| 4.5 | 396 | 1.93 | 2.42 | 2.90 | 3.39 | 3.87 |
| 5.0 | 440 | 2.15 | 2.69 | 3.23 | 3.77 | 4.31 |
| 5.5 | 484 | 2.37 | 2.96 | 3.55 | 4.14 | 4.74 |
| 6.0 | 528 | 2.58 | 3.23 | 3.87 | 4.52 | 5.17 |
| 6.5 | 572 | 2.80 | 3.50 | 4.20 | 4.90 | 5.60 |
| 7.0 | 616 | 3.01 | 3.77 | 4.52 | 5.28 | 6.03 |
| 7.5 | 660 | 3.23 | 4.04 | 4.84 | 5.65 | 6.46 |
| 8.0 | 704 | 3.44 | 4.31 | 5.17 | 6.03 | 6.89 |
| 8.5 | 748 | 3.66 | 4.57 | 5.49 | 6.41 | 7.32 |
| 9.0 | 792 | 3.87 | 4.84 | 5.81 | 6.78 | 7.75 |
| 9.5 | 836 | 4.09 | 5.11 | 6.14 | 7.16 | 8.18 |
| 10.0 | 880 | 4.31 | 5.38 | 6.46 | 7.54 | 8.62 |

This answer is also the ounces per minute one should catch from each spray nozzle on the system 20 to simulate the selected tractor sprayer's conditions.

8. Determine operating line pressure in the line recycling fluid back to the reservoir.

EXAMPLE 1a

Broadcast Spraying

Assume for the tractor sprayer:
The speed is 2 mph or 176 feet per minute.
The gallons per acre required is 20.
Referring to Table I, the factor is 0.86.
The distance between nozzles is 20 inches.
Note: 0.86×20=17.2. Therefore, one should catch 17.2 ounces per minute per nozzle to apply 20 gallons per acre. Therefore, to simulate the field conditions, one should also catch 17.2 ounces per minute per nozzle on the system 20.

To make major changes in the output of either the tractor sprayer or the system 20, change either the reservoir nozzle tip(s) or the spray nozzle tip(s). Large changes in reservoir line pressure should be avoided in the system 20 for accuracy. A nozzle chart should be used to select a nozzle with the correct capacity at a pressure of approximately 30 pounds per square inch in order to match typical commerical practices.

EXAMPLE 1b

Band Spraying

Assume for the tractor sprayer:
The speed is 2 mph or 176 feet per minute.
The band width is 14 inches.
Referring to Table I the factor is 0.86.
The gallons per acre required is 20 (broadcast basis).
Note: 0.86×14=12.04 ounces. Therefore, one should catch 12.04 ounces per minute per nozzle to correctly apply 20 gallons (broadcast) in a 14-inch band, and one should also catch 12.04 ounces per minute per nozzle on the lab sprayer (system 20) to simulate the field conditions.

The pump used in system 20 for these Examples is available commercially from Eastern Industries Pump Products Division, Hamden, Conn. as a P-7 pump.

To determine the amount of chemical to put into the reservoir of the system 20, divide the number of gallons the tractor sprayer reservoir holds by the number of gallons such sprayer applies per acre. Multiply this figure by the quantity of chemicals to be applied per acre by the tractor sprayer. For example, if the tank holds 100 gallons, and the sprayer applies 20 gallons per acre, and four quarts of chemical are required per acre, then:

$$\frac{100 \text{ gallon spray tank}}{20 \text{ gallons per acre}} \times 4 \text{ quarts/acre} = 20 \text{ quarts per spray tank.}$$

Now, since the tractor sprayer tank holds 100 gallons, then:

$$\frac{20 \text{ quarts per tankful}}{100 \text{ gallons per tankful}} = 0.2 \text{ quarts per gallon, or 25.6 ounces of chemicals per gallon in the system 20 reservoir.}$$

Once system 20 is calibrated for band spraying, one adds the same amount of chemical to the system 20 as if one were broadcasting.

EXAMPLE 2

As those skilled in this art appreciate, if proper mixing procedures are not followed when preparing a tank mix, the chemicals to be sprayed will separate in the tank or form clumps which are practically impossible to get into aqueous suspension. For example, when a combination of "Lasso" TM and atrazine are not properly mixed, they may separate with the atrazine settling to the bottom of the system 20 reservoir and the "Lasso" TM floating to the top thereof. This result will cause a heavy atrazine application rate at the start of a commercial spraying operation and a heavy "Lasso" TM rate near the end of such spraying operation.

Procedural steps for using system 20:
1. Use a clean spray reservoir, which is internally free of oily film. Fill ⅔ full of water. In this embodiment, the reservoir has a total capacity of about one gallon.
2. Set the system 20 to 30 psi with full recirculation. Read between 4 and 9 inches of vacuum (a higher reading would indicate that the isolation valve is not fully open and/or that the filter is blocked).

3. Slurry the wettable powder to be tested (e.g. a herbicide or the like); do not over mix. Pour slurry into the reservoir with the agitator running and allow to mix thoroughly. If a slurry is not prepared first, the wettable powder may float on top of the spray tank and is very difficult to mix. Note any increase in vacuum because there should be a steady state vacuum at each stage of material addition.

4. Mix one part emulsifiable concentrate to be tested (such as "Lasso" TM) with two parts water in a clean beaker (or an equivalent), and add to the system 20 reservoir with recirculation operating. This step ensures a good mixture of the emulsifying agent and the active chemical so they are evenly dispersed as added to the system 20 reservoir. Note any increase in vacuum for the reason above noted.

5. Fill the remainder of the tank with water.

This above procedure is the currently preferred way to get a good mixture for testing in system 20.

Typically, one should be able to recirculate such a test mixture for several minutes without any substantial increase in system 20 vacuum. A total increase of about 5 inches vacuum above the system 20 normal is considered acceptable. Larger increases generally indicate possible problems of screen plugging in a full scale sprayer.

Next, turn the system 20 spray nozzle ball valve 65 full on. One typically sees about 1 to 4 pound pressure drop with about 1 to 4 inch vacuum increase indicating an increased flow rate from the reservoir 28. Measure this flow rate from the spray nozzle 53 initially and at about half a reservoir. This flow rate typically is between about 27 to 32 ounces per minute. The respective two flow rates should typically not vary by more than about 0.3 ounces per minute. Larger variances indicate possible plugging of the filter screen 47.

Exemplary combinations each of which make a good system 20 reservoir mix for testing and evaluating using this procedure under normal conditions are as follows:

"Lasso" TM —"Lorox" TM
"Sutan+" TM —atrazine Liquid or wettable powder
"Sutan+" TM —"Bladex" TM
"Lasso" TM —"Lexone" TM
"Lasso" TM —atrazine Liquid or wettable powder
"Lasso" TM —"Sencor" TM
"Treflan" TM —"Sencor" TM
"Treflan" TM —"Lexone" TM Lasso: is Monsanto Company trademark for their Alachlor formulation
Lorox: is E. I. duPont de Nemours & Co., Inc. trademark for their Linvron formulation
Sutan+: is Stauffer Chemical's trademark for their Butylate plus inert herbicide safener R-25788 formulation. R-25788 is Stauffer Chemical's trademark for their herbicide safener.
Bladex: is Shell Chemical Company's trademark for their Cyanazine formulation
Lexone: is E. I. duPont de Nemours & Co., Inc. trademark for their Metribuzin formulation
Sencor: is Mobay Chemical Corporation trademark for their Metribuzin formulation
Treflan: is Elanco Products trademark for their Trifluralin formulation.

Note: If these steps are followed, and one still has problems with chemical separation, the agitation may be excessive.

On rare occasions when preparing a reservoir mix for system 20, the chemicals will clump together and are then practically impossible to get into solution or dispersion. To clean such chemicals from the system 20, fill the reservoir full of water and add a detergent such as "Spic 'N Span" TM (available from Procter and Gamble Company) while running the recirculation system. Before trying to use such a reservoir mix again, it is preferred to check its compatibility with a ball jar test.

A system 20 should be cleaned before being stored or before another chemical is to be tested in such system 20. Check each label of each sprayable concentrate for any special cleaning procedures suggested by its manufacturer.

In cleaning, add one teaspoonful of detergent per gallon of water, for example, depending on strength of detergent. Close valve 65 to spray boom, open by-pass valve 67 and agitate vigorously for 10 to 15 minutes. Drain reservoir. Use hose to rinse down inside of reservoir. Repeat procedure, but instead of draining reservoir, open spray boom to flush tank-cleaner/water solution out of reservoir. For sprayers being reused immediately, refill reservoir with water, open spray boom valve and empty reservoir by spraying through boom nozzles. For sprayers being stored, do not use rinse after treatment.

EXAMPLE 3

Some liquid fertilizers and herbicides do not mix well and cannot be applied together using system 20. One can check the compatibility of a fertilizer and a herbicide with the following test procedure:

1. Fill clean reservoir with ⅔ gallon of liquid fertilizer.
2. Set the system 20 to 30 psi with full recirculation. One should read between 4 to 9 inches of vacuum.
3. Premix wettable powders or combinations with herbicides before addition to fertilizer.
4. Fill reservoir with balance of fertilizer.
5. Allow to recirculate for several minutes. Note any increase in vacuum. An increase of 5 inches above the initial is acceptable. Larger increases would indicate possible problems of screen plugging. If large increases in vacuum are noted or obvious compatibility problems are noted, discontinue test. Clean system 20 and repeat procedure, but before adding any wettable powders or herbicides, add the recommended amount (about 1%) of a compatibility agent, such as "Kombind" TM, "Compex" TM, "Unite" TM, or the like. If no problems are encountered, continue with step 6. This procedure is used to prepare each of the mixtures shown below in Table II.
6. Turn the spray valve full on (note the decrease in pressure and increase in vacuum).
7. Collect several 100 ml portions from start of reservoir to end of reservoir.
8. Stopper cylinders and allow to stand for two hours.
9. The initial cylinder and final cylinder should have equal amounts of separations. If not, the recirculation is insufficient to use this combination.

Table II below provides examples of combinations which require a compatibility agent (e.g. an organo phosphate ester, a sulfosuccinate, or the like) together with use conditions for achieving compatibility thereof in a system 20.

TABLE II

RATE TABLE FOR TESTING COMPATIBILITY
AMOUNT OF HERBICIDE TO BE ADDED TO ONE PINT OF LIQUID FERTILIZER

| Gallons of Fertilizer To Be Applied Per Acre | 6.7# A.I./gal. Example: Sultan + | | 4#/gal. Example: Lasso | 65 WP Example: Ramrod or Ramrod/Atrazine | 80 WP Example: Atrazine or Bladex | |
|---|---|---|---|---|---|---|
| | 3.75 pt./Acre teaspoons | 4.75 pt./Acre teaspoons | 2½ qt./Acre teaspoons | 6#/Acre teaspoons | 1#/Acre teaspoons | 1.6#/Acre teaspoons |
| 10 | 1.5 | 2 | 2 | 7 | 2 | 3 |
| 15 | 1.0 | 1.5 | 1.5 | 5¼ | 1½ | 2 |
| 20 | .75 | 1 | 1 | 3½ | 1 | 1½ |
| 25 | .6 | .75 | .75 | 3 | ¾ | 1¼ |
| 30 | .5 | .6 | .6 | 2½ | ⅝ | 1 |
| 40 | .4 | .5 | .5 | 1¼ | ½ | ¾ |

Use ½ teaspoon Compex for every rate of application.
Other rates may be interpolated from the table.

Studies of system 20 may utilize information on particle sizes of common granular biocides. Therefore the following illustrative information is provided:

TABLE III

MESH SIZES OF COMMON GRANULAR HERBICIDES AND INSECTICIDES

| Herbicides | | Insecticides | |
|---|---|---|---|
| Aatram | 20–50 | Counter 15G | 24–48 |
| Amiben 10G | 24–48 | Diazinon 14G | 15–30 |
| Bladex 15G | 20–60 | Dyfonate 20G | 20–40 |
| Eptam | 20–40 | Furdan 10G | 20–40 |
| Knoxweed | 20–40 | Heptachlor 20G | 15–30 |
| Lasso II | 24–48 | Thimet 15G | 24–48 |
| Lasso-Atrazine | 24–48 | | |
| Ramrod 20G | 24–48 | | |
| Randox 20G | 20–40 | | |
| Randox-T G | 20–40 | | |
| Sutan 10G | 20–40 | | |
| Sutan-Atrazine 18-6 | 20–40 | | |
| Treflan 5G | 30–60 | | |
| Vernam 10G | 20–60 | | |

In the above examples, the nozzles used in reservoir 28 were as follows (together with operating characteristics):

TABLE IV

I 8003 TEEJET NOZZLE
Equivalent Orifice Diameter .043"

| Liquid Pressure in PSI | Capacity 1 Nozzle in Oz./Min. | Gallons Applied Per Acre at: | | | |
|---|---|---|---|---|---|
| | | 4 MPH | 5 MPH | 7.5 MPH | 10 MPH |
| 20 | 26.88 | 15.7 | 12.6 | 8.4 | 6.3 |
| 25 | 30.72 | 17.6 | 14.1 | 9.4 | 7.1 |
| 30 | 33.28 | 19.0 | 15.4 | 10.3 | 7.7 |
| 40 | 38.40 | 22.0 | 17.8 | 11.8 | 8.9 |
| 50 | 43.54 | 25.0 | 20.0 | 13.2 | 10.0 |
| 60 | 47.36 | 27.0 | 22.0 | 14.4 | 10.9 |

| SPRAY ANGLE: | 20 PSI | 40 PSI | 80 PSI | 200 PSI |
|---|---|---|---|---|
| 8003 TEEJET | 70° | 80° | 87° | 90° |
| H ¼ U003 VEEJET | | 0° Solid Stream | | |

II H ¼ U003 VEEJET NOZZLE
Equivalent Orifice Diameter .046"

| Liquid Pressure in PSI | Capacity 1 Nozzle in Oz./Min. |
|---|---|
| 5 | 14.08 |
| 10 | 19.20 |
| 20 | 26.88 |
| 25 | 30.72 |
| 30 | 33.28 |
| 40 | 38.40 |

The distance between the nozzle and the output orifice was about 60 centimeters.

EXAMPLE 4

System 20 reservoir 28 of one gallon capacity is filled with ⅔ of a gallon of tap water. The orifice size in the agitation head on the recirculation line in the system 20 reservoir is 0.032" in diameter. Valves 67, 68 and 69 are full open and valve 65 is fully closed. The pum 21 and motor 25 are turned on and the speed of motor 25 is adjusted with rheostat 26 to produce 50 psig on guage 70. In a beaker, 10 grams of Ca(OH)$_2$ is slurried with 150 grams of tap water. This slurry is then added to the system 20 reservoir through hole 42. The pressure shown on guage 70 is maintained at 50 psig for 10 minutes and degree of agitation in reservoir 28 is observed using tick marks as outlined above. The pressure is then reduced to 40 psig as shown on guage 70 and maintained for 10 minutes. Again observation is made as outlined above. This sequence is repeated. Pressure is then reduced 10 psig and recirculation maintained for 10 minutes and degree of agitation is observed as outlined above until zero psig is attained. Then the reservoir is drained and cleaned out. The orifice size is changed to 0.043" in diameter and the entire process outlined above is repeated for this new orifice size.

Those skilled in the art will appreciate that this procedure can be repeated for any number of orifice sizes desired. As it will be noted from this example, as soon as the recirculation is stopped, the Ca(OH)$_2$ quickly precipitates out of solution. When the agitation is then reinitiated, it is very difficult to reincorporate or disperse the Ca(OH)$_2$ in the water to the homogeneous state as it was initially even applying maximum agitation in system 20 because of particle adherence to wet interior system 20 surfaces.

In order to effect a stable suspension, it is necessary to add a surfactant by utilizing a burette, syringe, or the like. A surfactant can be added incrementally over a period of time until a stable suspension is obtained. For example, the reservoir 28 is filled ⅔ full of tap water and 30 grams of Ca(OH)$_2$ slurried and added to the reservoir 28, as explained above. Recirculation is maintained for two minutes. Now valve 65 is opened and a 100 ml portion is collected in a graduated cylinder. Next, to the reservoir is added 1 ml of a surfactant which is here comprised of 10 mole ethoxylate nonylphenol. Agitation is maintained for two minutes and again valve 65 is opened to collect a 100 portion. This process if repeated until the reservoir 28 is nearly empty or until it is noted that the 100 ml samples of $Ca(OH)_2$ slurry have reached a stable state. It will be seen that approximately 8 ml of such 10 mole ethoxylate nonylphenol is needed to produce a slurry of $Ca(OH)_2$ that will remain stable for several minutes. Such a stability time in a system 20 can be considered to be at least generally sufficient for a larger scale corresponding composition to be sprayed from a commercial scale (large) spray apparatus.

Now the reservoir 28 is cleaned out and filled ⅔ full of tap water to which is added 30 grams of $Ca(OH)_2$ slurry as explained above. However, to this water is added 8 grams of 10 mole ethoxylate nonylphenol. Recirculation is maintained for 10 minutes after which it is turned off. If allowed to stand unagitated for one hour or more, it will be observed that the $Ca(OH)_2$ will again settle to the bottom of the reservoir. Now, however, when recirculation is resumed, the $Ca(OH)_2$ will redisperse easily with minimum agitation to reform a homogeneous mixture.

As one skilled in the art will appreciate, this system constitutes, for example, a viable solid suspension in water suitable for applying through a full scale tractor sprayer or the like.

EXAMPLE 5

3,5-dinitro-$N^4$, $N^4$-dipropylsulfanilamide is obtained as a powder with a maximum particle size smaller than 50 microns. The system 20 reservoir is filled with ⅜ of a gallon of water and recirculation is maintained at 40 psig with a 0.043" diameter orifice on the agitation head of the recirculation line in the reservoir. 21 grams of 3,5-dinitro-$N^4$, $N^4$-dipropylsulfanilamide is slurried in 100 grams of tap water in a beaker and added to system 20 reservoir while recirculation is maintained as described above. Recirculation is continued for 2 minutes after which valve 65 is opened and a 100 ml portion of suspension is collected in a graduated cylinder. Next, 1.0 ml of a 50/50 mixture of calcium dodecylbenzene sulfonate and a fourteen mole ethoxylate of nonylphenol is added. Recirculation is maintained for two minutes after which a 100 ml portion is again taken. This process of adding 1.0 grams of surfactant, recirculating for two minutes, and taking a 100 ml portion in a graduated cylinder is repeated until a total of 8 grams of surfactant has been added to the system 20 reservoir. The graduated cylinder containing the series of 100 ml portions of suspended solids are observed for a period of one hour. It is noted that an initial portion, with no added surfactant, shows a separation of about 3 ml in volume floating at the top of a first cylinder. A second portion, with 1.0 gram of added surfactant, only shows about 0.5 ml of separation in another cylinder, and it was noted that the fluid above such separation is much darker and more uniform than that of such first cylinder. The separation is observed at the bottom of the cylinder further exemplifying the enhanced suspension of the solids.

In conjunction with these observations, it is noted that upon addition of the 8th gram of surfactant and its two minute recirculation period, there is no longer any undispersed solid remaining in the reservoir of the system 20.

EXAMPLE 6

The system 20 reservoir is filled with ⅜ of a gallon of water and recirculation is obtained with 30 psig and a 0.043" diameter orifice on the agitation head of the recirculation line in the system 20 reservoir. While being so agitated, 100 ml of 0,0-dimethyl S-(1,2-dicarbethoxyethyl) phosphorodithioate 96% actives as a liquid is added to the reservoir of the system 20. Recirculation is maintained for 2 minutes and a 100 ml portion is collected in a graduated cylinder as before. It is observed that within the 2 minute recirculation period without added surfactant, the above-mentioned oily liquid stayed moving around within the reservoir. Obviously this is a nonhomogeneous mixture. After the 100 ml portion is taken, 1.0 ml of a 50/50 mixture of calcium dodecylbenzene sulfonate and a 14 mole ethoxylated nonylphenol is added. Recirculation is continued for 2 minutes and another 100 ml portion is collected. This procedure is repeated as previously described until a total of 8 ml of surfactant is added to the reservoir. It is observed that during this process, the oil globules initially visible progressively disappear until a homogeneous emulsion is obtained wherein the droplet size is estimated to be not more than about 50 microns. Upon observing the successively collected cylinders of emulsions, it is noted that the first portion in a first cylinder shows 1.0 ml of oily separation while a second portion in a second cylinder shows 0.2 ml of a heavy cream which is easily redispersed. A third portion in a third cylinder contains 0.1 ml of such cream which a fourth portion in a fourth cylinder shows no separation.

I claim:

1. A test apparatus for duplicating on a miniature scale the behavior of a commercial scale spray apparatus to evaluate behavior of specific sprayable systems under generally controlled conditions, said apparatus comprising:

(A) pump means for pumping a sprayable fluid through said test apparatus having a generally uniform volumetric output of fluid at a predetermined fluid output pressure, said pump means having pump input and output means, (B) variable drive means associated with said pump means for varying the volumetric output of fluid from said pump, (C) reservoir means having an elongated interior configuration and having reservoirs inlet and outlet means, said outlet means being located in a gravitationally lowermost region of said reservoir means, (D) orifice means associated with said reservoir inlet means and adapted to discharge generally into the interior gravitationally bottom region of said reservoir means, (E) filter means for separating particulate material over a predetermined maximum particle size from a fluid past therethrough, said filter means having filter input and output means, (F) nozzle means for spraying a predetermined volume of said pumped sprayable fluid, (G) first tube means interconnecting said pump means with said orifice means, (H) second tube means interconnecting said reservoir outlet means with said filter input means, (I) third tube means interconnecting said filter output means with said pump input means, (J) fourth tube means interconnecting a predetermined location in said first tube means with said nozzle means, (K) first pressure sensing means associated with said first tube means for measuring fluid pressure therein, (L) second pressure sensing means associated with said filter means for measuring fluid pressure in the region of said filter output means, (M) means for introducing a fluid into said reservoir, (N) first valve means located in said fourth tube means for controlling flow through said fourth tube means, (O) second valve means located in said first tube means between said predetermined location and said orifice means for regulating flow through said first tube means, (P) the distance between said reservoir inlet means and outlet means in said reservoir means being not more than about 50 centimeters, (Q) the aperture of said orifice means being not greater than about 0.5 square centimeters, (R) said reservoir means including means for evaluating the contents thereof during operation of said test apparatus.

2. The test apparatus of claim 1 wherein third and fourth valve means are associated with said filter input and output means for isolating when desired said filter means from its associated respective second and third tube means.

3. A process for evaluating on a miniature scale the sprayability behavior of a specific sprayable aqueous composition in a selected full-scale spray apparatus, said process comprising the steps of:

(A) mixing the non-aqueous components of at least one sprayable composition with a desired quantity of water in an elongated reservoir, said mixing being achieved by the substeps of removing minor portions of the resulting mixture from a first gravitationally bottom region of said reservoir and injecting such minor portions under pressure through a nozzle member positioned in a second gravitationally bottom region of said reservoir which second region is in longitudinally spaced relationship to said first region relative to said reservoir, said reservoir having an internal length ranging from about 10 to 50 centimeters, and having an internal volume ranging from about 1 to 6 liters, said nozzle member having a cross-sectional area in its region of maximum constriction which is less than about 0.5 square centimeters, (B) determining the extent of mixing occuring in said reservoir for a given nozzle member cross-sectional area and for at least one selected said nozzle pressure in the range from about 20 to 60 pounds per square inch gauge after a predetermined mixing time interval, and (C) correlating said extent of mixing so determined with the extent of mixing achieved in said selected full-scale spray apparatus wherein the comparable nozzle member has a cross-sectional area greater than about 0.5 square centimeters and wherein the comparable reservoir member has an internal length greater than about 50 centimeters and an internal volume greater than about 6 liters.

4. The process of claim 3 wherein said step (B) is repeated a plurality of individual times, each respective repeat being conducted at a different generally constant said nozzle pressure and that estimated nozzle pressure which is sufficient to produce substantial homogeneity in the resulting so-mixed mixture is determined.

5. The process of claim 3 wherein said determination is made while maintaining said nozzle pressure at a pressure ranging from about 20 to 40 pounds per square inch gauge.

6. The process of claim 4 wherein said sufficient pressure is determined by comparing each such individual repeat nozzle pressure to the extent of mixture mixing achieved at such pressure at the end of said mixing time interval, and interpolating the results so obtained to estimate the pressure required to obtain said substantial homogeneity.

7. The process of claim 4 wherein the extent of mixing at each said nozzle pressure is determined by optical inspection of the interior of said reservoir.

8. The process of claim 7 wherein said repeating is carried out by starting with a predetermined upper said pressure within said pressure range, and thereafter gradually decreasing said upper pressure incrementally to respective lower pressures at a time rate of decrease ranging from about 2 to 10 pounds per square inch gauge per minute until a pressure is reached where the liquid phase of said mixture in said reservoir optically appears to be substantially non-homogeneous.

9. The process of claim 8 wherein after said correlation is completed, it is found that said full scale spray apparatus has a nozzle size which is larger than that needed to produce a substantially completely homogeneous mixture and wherein, in order to determine whether such larger sized nozzle will produce a substantially homogeneous mixture which is sprayable. The following procedural steps are employed:

(A) correlating the nozzle size in the full-scale spray apparatus with the nozzle cross-sectional area of said nozzle member in said reservoir, (B) correlating such nozzle size with line pressure, (C) mixing said sprayable composition in said reservoir with said nozzle member at said nozzle pressure and observing whether or not a sprayable homogeneous mixture is produced.

10. The process of claim 4 wherein said sufficient pressure for said given nozzle member cross-sectional area is correlated with the same corresponding pressure in said full-scale spray apparatus and which an equivalent larger sized nozzle member needed in said full-scale spray apparatus to produce a said mixture therein which has said substantial homogeneity.

11. A process for evaluating on a miniature scale the sprayability behavior of a specific sprayable aqueous composition from a selected full-scale spray apparatus comprising the steps of:

(A) continuously removing incremental portions of a substantially completely homogeneous aqueous sprayable composition from one region inside a reservoir, (B) continuously pressurizing one fraction of said so removed incremental portions and injecting such so pressurized one fraction through a nozzle member located in said reservoir at a second region inside said reservoir, said second region in spaced relationship to said one region, the relationship between said pressure and the orifice of said nozzle member being such as to produce in said reservoir a mixing action in said aqueous sprayable composition which is initially assumed to be at least sufficient to maintain the liquid phase contents of said reservoir in its substantially completely homogeneous condition, (C) continuously pressurizing the remaining fraction of said so removed incremental portions and ejecting such so pressurized remaining fraction through a spray head, (D) first collecting at least one first sample of such aqueous sprayable composition as so ejected through said spray head at a preselected starting time, (E) secondly collecting at least one subsequent sample of such aqueous sprayable composition as so ejected through said spray head at a predetermined end time after said starting time, (F) first measuring the degree of settling associated with said first sample after a measured time interval, (G) secondly measuring the degree of settling associated with said subsequent sample after a measured time interval, (H) comparing said first measured degree to said subsequent measured degree to generate a ratio.

12. The process of claim 11 wherein, when said ratio is a value other than unity, a measurement is made of the amount of increased pressure required in pressurizing said one fraction over said initially assumed value to cause said ratio to return to a value of unity.

13. A process for evaluating on a miniature scale the quantity of additive material necessary to achieve homogeneity of a sprayable aqueous composition, said method comprising the steps of:

(A) continuously mixing the non-aqueous components of at least one sprayable composition with a desired quantity of water in an elongated reservoir, said mixing being achieved by the sub-steps of removing minor portions of the resulting mixture from a first gravitationally bottom region of said reservoir and injecting such minor portions under pressure through a nozzle member positioned in a second gravitationally bottom region of said reservoir, which said second region is in longitudinally spaced relationship to said first region relative to said reservoir, said reservoir having an internal length ranging from about 10 to 50 centimeters, and having an internal volume ranging from about 1 to 6 liters, said nozzle member having a cross-sectional area in its region of maximum constriction which is less than about 0.5 square centimeters, (B) adding to said elongated reservoir while said mixing is occuring a predetermined material at a predetermined rate of addition, said rate of addition being such that said material so added becomes substantially completing mixed with said mixture of said sprayable composition and said water in said reservoir within a total time interval which is not greater than about that time which is necessary to achieve a cumulative removal of said resulting mixture from said reservoir which is equal to the total volume of said mixture in said reservoir, (C) sensing the extent of homogeneity in said reservoir of the combination of said resulting mixture and added material and (D) stopping said adding while maintaining said mixing when said sensing shows that the combination of said resulting mixture and said added material has reached at least a predetermined level of uniformity.

14. The process of claim 13 wherein said level of uniformity is substantially homogeneous.

15. The process of claim 13 wherein the total volume of said resulting mixture in said reservoir is not more than about 6 liters and wherein said mixing is conducted at a turnover rate which is not greater than about 5 minutes.

* * * * *